United States Patent
Buchanan

(10) Patent No.: US 11,628,287 B2
(45) Date of Patent: *Apr. 18, 2023

(54) SYSTEM FOR ENHANCED SEALING OF COUPLED CONNECTORS

(71) Applicant: BLUE I.V. LLC, West Nyack, NY (US)

(72) Inventor: Sheila Buchanan, West Nyack, NY (US)

(73) Assignee: BLUE I.V. LLC, West Nyack, NY (US)

(*) Notice: Subject to any disclaimer, the term of this patent is extended or adjusted under 35 U.S.C. 154(b) by 91 days.

This patent is subject to a terminal disclaimer.

(21) Appl. No.: 16/518,954

(22) Filed: Jul. 22, 2019

(65) Prior Publication Data

US 2019/0344064 A1 Nov. 14, 2019

Related U.S. Application Data

(63) Continuation of application No. 15/673,027, filed on Aug. 9, 2017, now Pat. No. 10,357,643.

(60) Provisional application No. 62/455,359, filed on Feb. 6, 2017.

(51) Int. Cl.
*A61M 39/10* (2006.01)
*A61M 39/20* (2006.01)

(52) U.S. Cl.
CPC ...... *A61M 39/105* (2013.01); *A61M 39/1011* (2013.01); *A61M 39/20* (2013.01); *A61M 2039/1027* (2013.01); *A61M 2039/1033* (2013.01); *A61M 2039/1088* (2013.01)

(58) Field of Classification Search
CPC .. A61M 39/10; A61M 39/162; A61M 39/105; A61M 2039/1033; A61M 2039/1038; A61M 2039/1088; A61M 2039/1044; A61M 2039/1072
See application file for complete search history.

(56) References Cited

U.S. PATENT DOCUMENTS

| | | |
|---|---|---|
| 4,076,023 A | 2/1978 | Martinez |
| 4,993,133 A | 2/1991 | Goeserich |
| 5,047,021 A | 9/1991 | Utterberg |
| 5,230,706 A | 7/1993 | Duquette |
| 5,536,258 A * | 7/1996 | Folden ............... A61M 39/16 604/265 |
| 5,700,248 A | 12/1997 | Lopez |
| 6,682,509 B2 * | 1/2004 | Lopez ................ A61M 5/14 604/905 |
| 7,004,934 B2 | 2/2006 | Vaillancourt |
| 8,083,237 B2 | 12/2011 | Smith |
| 10,357,643 B2 * | 7/2019 | Buchanan ......... A61M 39/105 |

(Continued)

*Primary Examiner* — Laura A Bouchelle
(74) *Attorney, Agent, or Firm* — Cooper & Maersch LLC; Lorri W. Cooper

(57) ABSTRACT

A system for enhanced sealing of coupled medical lines includes a male fitting, a female fitting, and a flexible annular collar seal. The seal provides a sealing function to an open end of the connector. The male fitting is made of medical grade materials and includes a male connector fluidly coupled to a first line. The female fitting is made of medical grade materials and including a female connector fluidly coupled to a second line and configured to mate with the male connector. The seal is made of a medical grade polymer coupled to one or both the male fitting and the female fitting.

21 Claims, 5 Drawing Sheets

FIG. 3A

(56) References Cited

U.S. PATENT DOCUMENTS

| | | | |
|---|---|---|---|
| 2008/0021392 A1* | 1/2008 | Lurvey | A61M 39/16 604/111 |
| 2013/0331801 A1* | 12/2013 | Hoffman | A61M 39/12 604/272 |
| 2014/0100533 A1 | 4/2014 | Lyons | |
| 2014/0167411 A1 | 6/2014 | Kimbrell et al. | |

* cited by examiner

SYSTEM FOR ENHANCED SEALING OF COUPLED CONNECTORS

CROSS-REFERENCE TO RELATED APPLICATION

The present application is a continuation-in-part of U.S. patent application Ser. No. 15/673,027, filed on Aug. 9, 2017, now U.S. Pat. No. 10,357,643, issued on Jul. 23, 2019, which is related to and claims priority to U.S. Provisional Patent Application No. 62/455,359, filed Feb. 6, 2017, both of which are incorporated herein by reference in their entirety.

BACKGROUND

The present invention relates generally to the field of closure caps, seals or plugs for connectors or open ends of tubes of existing art and more specifically relates to medical fluid and medical line couplings. A luer connection is used in many types of medical connectors for connecting various parts together, such as fluid lines to other connectors. There are many different types of medical delivery systems that utilize luer locks and other types of connectors. These include, among others, drainage, vascular, enteral, respiratory, epidural, and intrathecal medical devices; needless connectors; and end caps, their components and accessories.

Many patients need medical lines inserted when seeking medical care or visiting the emergency room. Others may need medical treatment on an outpatient basis. In either case, patients may be required to keep a medical line in place over a period of days, weeks, or even longer. In an outpatient situation, patients need to maintain their personal hygiene by showering, bathing and the like, resulting in the medical lines and connectors being exposed to various contaminating fluids from these activities.

When a patient is in an emergency room or hospital setting, intravenous lines, drainage tubes, or other medical devices having openings may remain in place for extended periods due to varying perspectives on the frequency at which they should be changed. Within the medical community, there is currently lack of agreement as to when medical lines, such as intravenous lines and needleless connectors, should ideally be replaced to avoid contamination to a patient. It is very important to patient health that the intravenous line, or other medical devices, remain sanitary to remove or minimize the risk of a secondary infection.

Central line associated blood stream infections (CLABSI) are caused by contaminants such as air, liquid, microorganisms and other biological materials that enter the central line system. After contaminants have entered the system, patients are at significant risk for infection, sepsis, organ failure, and death. Hospitals incur increased costs and are required to report such incidents. Patients often must endure additional procedures that would otherwise be unnecessary. An effective method of prevention of these types of infections is needed.

U.S. Pat. No. 5,230,706 to Duquette relates to a bi-directional valve assembly used in needleless injection or infusion ports. The described bi-directional valve assembly used in needleless injection or infusion ports includes a bi-directional valve assembly disposed within an infusion system to permit the administration of an infusion solution without the use of a needle. The bi-directional valve assembly is a two-way spring valve which comprises: a spring means, a valve port, and a valve plunger having a sealing means and a conduit means disposed thereabout. The spring means is connected to the valve plunger in such a way as to permit the opening of the conduit means when the spring means is recoiled such that the sealing means is not in contact with the valve port. This permits the closing of the conduit means when the spring means is expanded such that the sealing means is in contact with the valve port; whereby the bi-directional valve assembly is capable of opening and closing the infusion system.

U.S. Pat. No. 5,047,021 to Utterberg relates to a male luer lock fitting that has an elongated nozzle and an internally threaded locking ring that is mounted around the nozzle. The locking ring has complete freedom to rotate about the nozzle axis, and limited freedom to translate along the nozzle axis. The nozzle and locking ring are designed to have relative dimensions which enable a user to disconnect the system easily from a female luer lock.

SUMMARY

In view of the foregoing disadvantages inherent in the art of medical fluid, vascular access, and drainage line couplings, the present disclosure provides a novel system for enhanced sealing of coupled medical fluid, vascular access, and drainage lines, as well as for other medical connectors.

BRIEF DESCRIPTION OF THE DRAWINGS

The various embodiments of the present invention will hereinafter be described in conjunction with the appended drawings, wherein like designations denote like elements.

DETAILED DESCRIPTION

Figure 1:
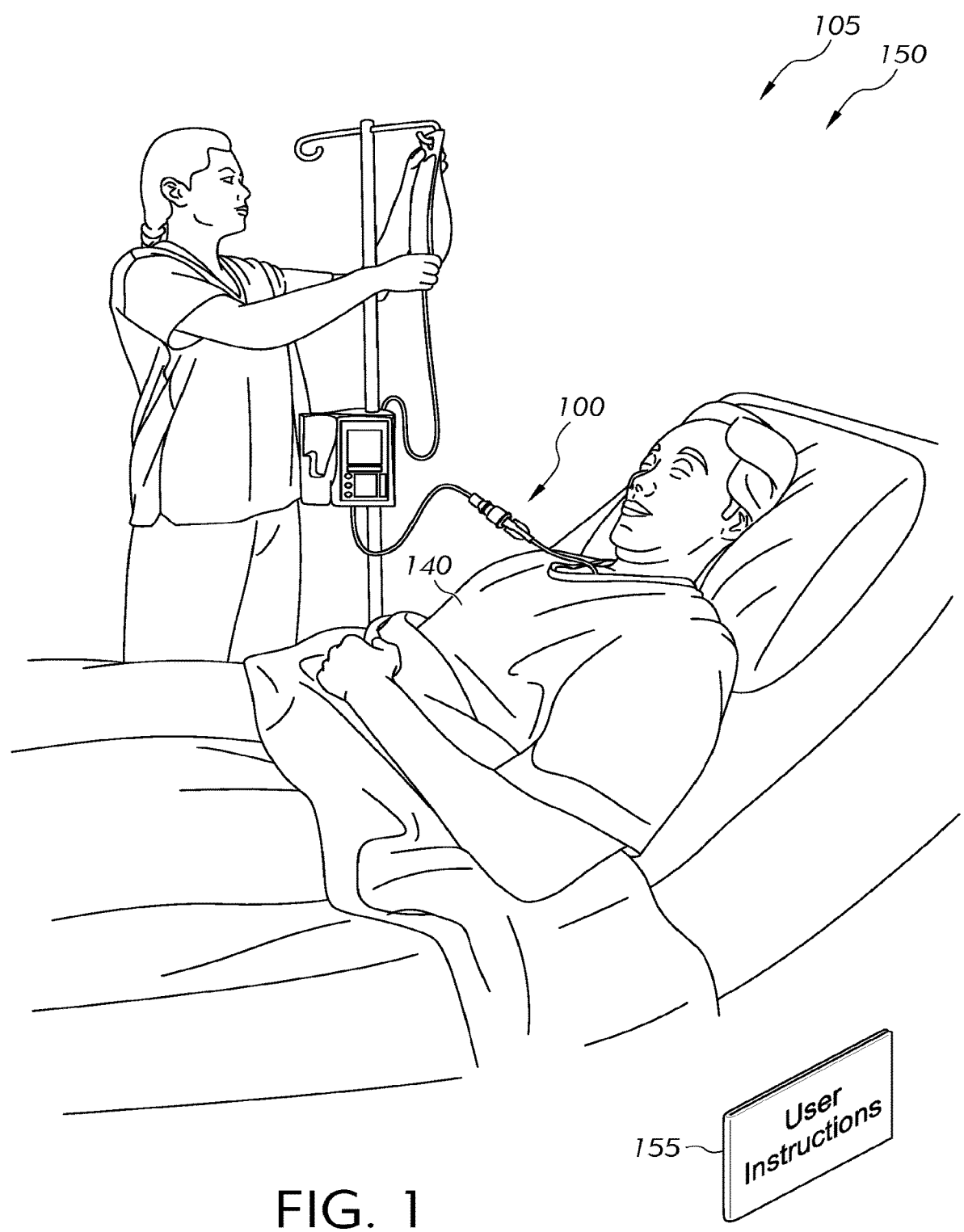
FIG. 1 is a perspective view of the system for enhanced sealing of coupled medical fluid lines during an 'in-use' condition, according to an embodiment of the disclosure.

As discussed above, embodiments of the present disclosure relate to medical couplings, including fluid and vascular access line couplings. The invention is useful in any type of fluid connection that utilizes a connector for connecting two parts. For example, the present invention allows direct or functional connection between delivery systems, including unrelated delivery systems, such as vascular, enteral, epidural, intrathecal, and drainage medical devices; needleless connectors; and end caps, as well as their components and other accessories. The present disclosure also relates to a system for enhanced sealing of coupled medical lines. Enhances sealing improves the coupling of medical lines to maintain a sterile connection.

A sterile connection is critical in preventing infections in patients requiring medical connections, or use of any vascular access, medical fluid or drainage system devices for extended periods. In particular, a sterile connection is critical in preventing Central Line Associated Blood Stream Infections (CLABSI) and other blood stream infections.

Vascular access devices are generally defined as tubing inserted into peripheral or central vessels, used primarily to administer fluids and medications, monitor pressures, and collect blood. Likewise, central lines are generally defined as intravenous lines that are inserted into large veins typically located in the neck or near the heart for therapeutic or diagnostic purposes. Central lines are used, for example, to administer medicines or fluids, or to withdraw blood. These lines inserted into larger vessels are particularly helpful in achieving faster rates of infusion of fluids or medication in emergency or intensive care settings. However, central line infections can be very dangerous because of their location.

The present invention provides for an improved seal for central lines, other intravenous connections, and other medical connections, to prevent or deter air, liquid, microorganisms, and other contaminants from entering the blood stream. The herein disclosed seal creates a substantially air-tight seal (or an air-tight seal) that deters the entry of liquid into any threaded medical device. The threaded medical device disclosed herein is described in connection with a luer connection, which is also known as a luer lock. Other types of medical connector designs may also derive a benefit from the seal described herein, including threaded fittings, lug fittings, swivel fittings, tube fittings, barb fittings, as well as other known fittings.

The examples described herein depict a luer lock, which is often used when requiring a sterile connection. However, the examples herein may alternatively be used in connection with other types of connectors, as discussed above. For purposes of the present disclosure, whenever the term "luer lock" is utilized in describing the invention, it should be understood that any type of connector may be substituted for a luer lock, with the term luer lock being defined as any type of connector, including, but not limited to a luer lock unless applicant specifically states that it is limited to luer locks.

The use of a seal to deter the entry of foreign matter into a connector will assist in reducing infections and other reportable incidents, and therefore hospital admission days. Most importantly, mortality rates will decrease. The seal deters everyday contaminants, such as shower water, emesis, urine, and stool from entering the bloodstream at exposed connection points. The present disclosure provides for improved sealing to maintain a sterile connection in medical device connections.

The present disclosure may be used with Luer lock fittings to connect a wide variety of vascular access, infusion systems, drainage systems or needleless connector devices, among other devices, to a hub. The catheter typically has a female end with a threaded or lug style locking element that is compatible to connect with the threaded collar of a male Luer lock.

If no intravenous fluid is required, the end of the catheter or central line hub may be capped off with a needleless connector utilizing the present disclosure. In other instances, the present disclosure may be used in conjunction with a needleless connector with a female end having a threaded or lug style locking element. This type of connector is compatible with the threaded collar of a male Luer lock.

The present disclosure may be fabricated for compatibility with current standards and requirements set forth by the International Standards Organization. ISO 594 is currently in use; however, ISO 80369-7 will supersede ISO 594 for medical equipment. The standard consists of eight separate tests as follows: 1 Gauging: A dimensional check is performed using a calibrated plug gauge; 2 Liquid Leakage: Ensures that the sample Luer does not leak when pressurized with water; 3 Air Leakage: Ensures that the sample Luer does not leak when a vacuum pressure is applied; 4 Separation Force: Ensures that the sample Luer remains attached to the reference fitting when an axial load is applied; 5 Ease of Assembly: Ensures that the sample Luer can be assembled with minimum axial force and torque; 6 Unscrewing Torque: Ensures that the sample Luer remains attached under a specific unscrewing (counter-clockwise) torque; 7 Resistance to Overriding: Ensures that the threads cannot be overridden by a specific screwing (clockwise) torque; 8 Stress Cracking: Ensures that the sample Luer does not crack when assembled for 48 hours.

A color-coding system may be used with the present disclosure in conjunction with colored intravenous lines for example, to identify various intravenous administrations for a given patient. More specifically, the annular collar seal may be color matched to tinted intravenous lines or other connectors to further assist with distinguishing between differing medications supplied to a patient, as one example.

Biocompatibility requirements for medical components are becoming increasingly stringent in order to prevent patient rejection, infection, and adverse effects such as allergic reactions. Vascular access devices (VADs) are one category of medical components which includes various types of devices which are inserted into veins via peripheral or central blood vessels for diagnostic or therapeutic reasons, such as blood sampling, administration of medication or fluids, and blood transfusions. To avoid the above-mentioned concerns with vascular access devices, they are overwhelmingly fabricated from medical grade polymers.

Medical grade, as used herein, is defined as a material, in this instance a polymeric material, which has been tested for biocompatibility and deemed appropriate to be used for medical applications. Medical grade polymers are specifically designed to be used in, on or in contact with the body. All raw materials, intermediate products, and finished products for medical grade use are manufactured with appropriate regulatory standards and in high enough purity such it can be used for medical purposes safely in patients.

In addition to use of medical grade polymers, all medical devices used in intravenous therapy require thorough sterilization. Sterilization involves using chemicals, temperature, gas and/or pressure to kill or inactivate all disease-causing bacteria, spores, fungi and viruses. The United States Food and Drug Administration (FDA) recognizes three categories of sterilization methods currently used to sterilize medical devices in manufacturing settings: Traditional, Non-traditional, and Novel Non-traditional. Examples of each are illustrated in Table 1 below.

TABLE 1

Examples of Sterilization Methods for
Medical Devices in Manufacturing Settings

| TRADITIONAL | NON-TRADITIONAL | NOVEL NON-TRADITIONAL |
|---|---|---|
| Dry Heat | Hydrogen Peroxide ($H_2O_2$)/ Gas Plasma | Chlorine Dioxide ($ClO_2$) |
| Moist Heat | Ozone ($O_3$) | Ethylene Oxide - ETO-in-a-bag (Diffusion method, Injection method) |
| ETO (fixed chamber) | | Pulsed Light |
| Radiation (gamma, E-beam) | | Microwave Radiation |
| | | Sound Waves |
| | | Vaporized Chemical Sterilant Systems (e.g. hydrogen peroxide, peracetic acid) |

Some traditional sterilization methods have been found to be unsuitable for medical products as these products cannot support high temperature sterilization processes. An alternative, often used process for sterilization utilizes Ethylene Oxide (EtO) gas with elevated temperature and humidity. This has become the preferred method for many medical products due to its relatively low processing temperatures of nominally 118 degrees Fahrenheit and relative humidity of approximately 65%. Materials selected for the system for enhanced sealing of coupled medical fluid lines, including those for the annular collar seal of the system should be done so with emphasis on corrugate strength and chemical stability over time to ensure compatibility with the sterilization procedures of Table 1, as well as any future processes developed for sterilization of medical products.

Referring now more specifically to the drawings by numerals of reference, there is shown in FIGS. 1-5, various views of a system for enhanced sealing of coupled medical fluid lines, 100.

FIG. 1 shows a system for enhanced sealing of coupled medical fluid and vascular access lines during an 'in-use' condition 150, according to an embodiment of the present disclosure. Here, the system for enhanced sealing of coupled medical fluid and vascular access lines (system 100) may be beneficial for use by a user 140 to maintain a more sealed connection over prolonged use of intravenous and vascular access lines in a patient. Ideally, this may potentially lead or aid in decreasing or mitigating central line and other blood stream related infection rates, as well as decreasing associated mortality rates.

According to one embodiment, the system for enhanced sealing of coupled medical fluid and vascular access lines 100 may be arranged as a kit 105. In particular, the system 100 may further include a set of instructions 155. The instructions 155 may detail functional relationships in relation to the structure of the system 100 such that the system for enhanced sealing of coupled medical fluid and vascular access lines 100 can be used, maintained, or the like, in a preferred manner.

Figure 2A:
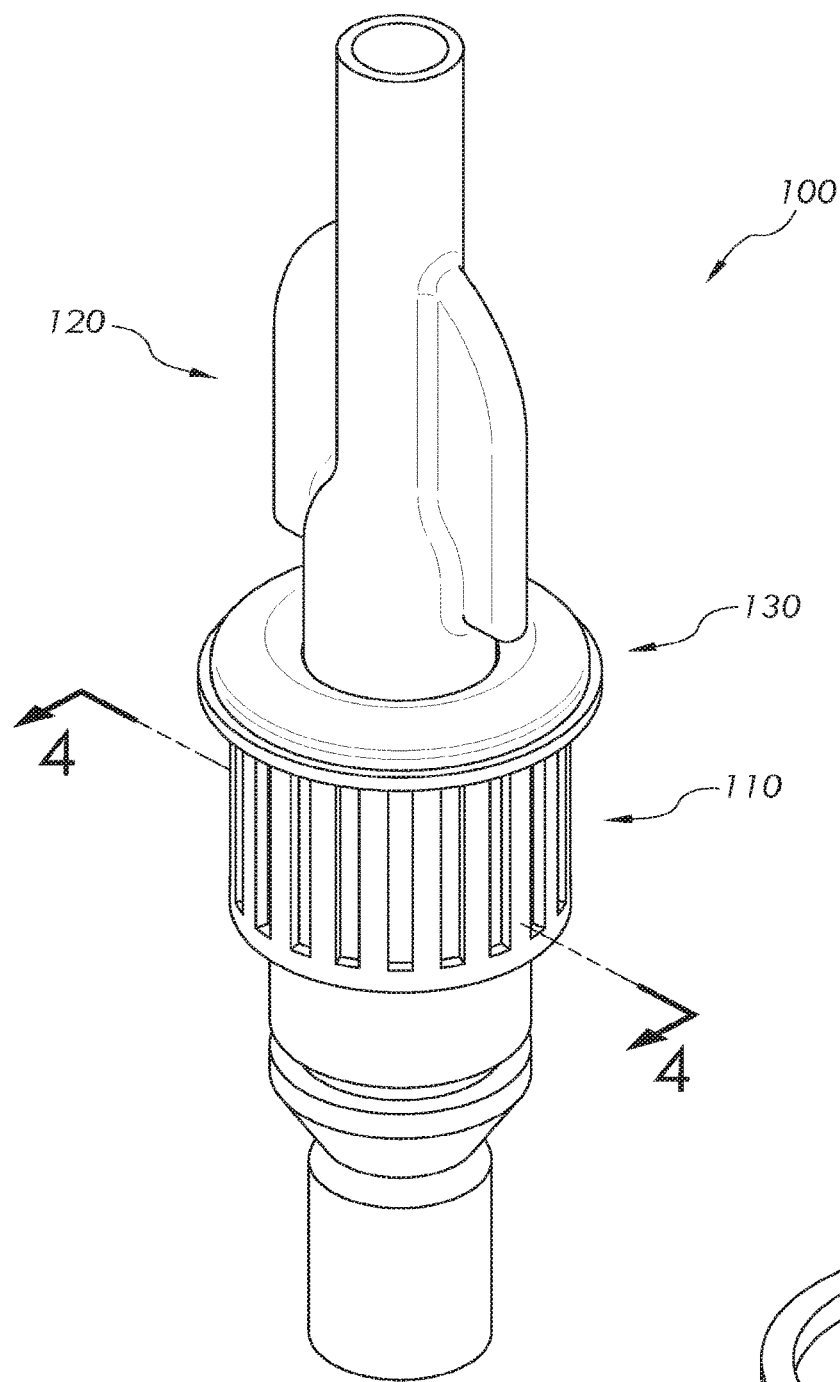
FIG. 2A is a perspective view of the system for enhanced sealing of coupled medical fluid and vascular access lines of FIG. 1, illustrating the male and female fittings, and the annular collar seal, according to an embodiment of the present disclosure.

FIG. 2A is a perspective view of the system for enhanced sealing of coupled medical fluid and vascular access lines of FIG. 1, illustrating example male and female fittings, and the annular collar seal, according to an embodiment of the present disclosure. As illustrated, the system 100 may include a male fitting 110, a female fitting 120, and an annular collar seal 130. The male fitting 110 may be made of rigid medical grade polymers. The female fitting 120 may be similarly made of rigid medical grade polymers. Also, the annular collar seal 130 may be made of non-rigid medical grade polymers. The seal 130 may be flexible.

The annular collar seal 130 may further be affixable to the male fitting 110. In particular, the annular collar seal 130 may be configured to further seal or otherwise provide a barrier around any male Luer lock connection, for example, that is part of a vascular access device or other medical device. Beneficially, the annular collar seal 130 may aid in preventing entry of contaminants such as shower water, emesis, urine, and stool into a patient's fluid delivery system. As such, the system 100 may aid in or be useful to maintain sterility of vascular access devices over time, and thereby reduce rates of infection as well as mortality rates in those patients requiring extended use of intravenous lines as part of treatment.

Figure 2B:
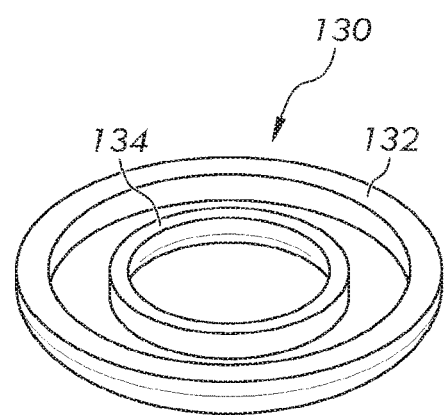
FIG. 2B is a detail view of the annular collar seal of the system for enhanced sealing of coupled medical fluid lines of FIG. 1, according to an embodiment of the present disclosure.

FIG. 2B is a perspective view of the annular collar seal 130 of FIG. 2A in isolation and from an interface perspective to illustrate the interior of the seal. As shown, the annular collar seal 130 may have an outer sealing lip 132 and an inner sealing lip 134, the outer sealing lip may be configured to circumscribe and seal against an outer perimeter of male fitting 110 (FIG. 2A), such as a locking collar 116 (FIG. 3A) of the male fitting 110. The inner sealing lip 134 may be configured to deformably permit passage of a male lock element 126 (FIG. 3A) of the female fitting 120 through the inner sealing lip 134 and into the locking collar 116, and further configured to seal against a connector guide 122 (FIG. 3A) after said passage of the male lock element 126.

Figure 3A:
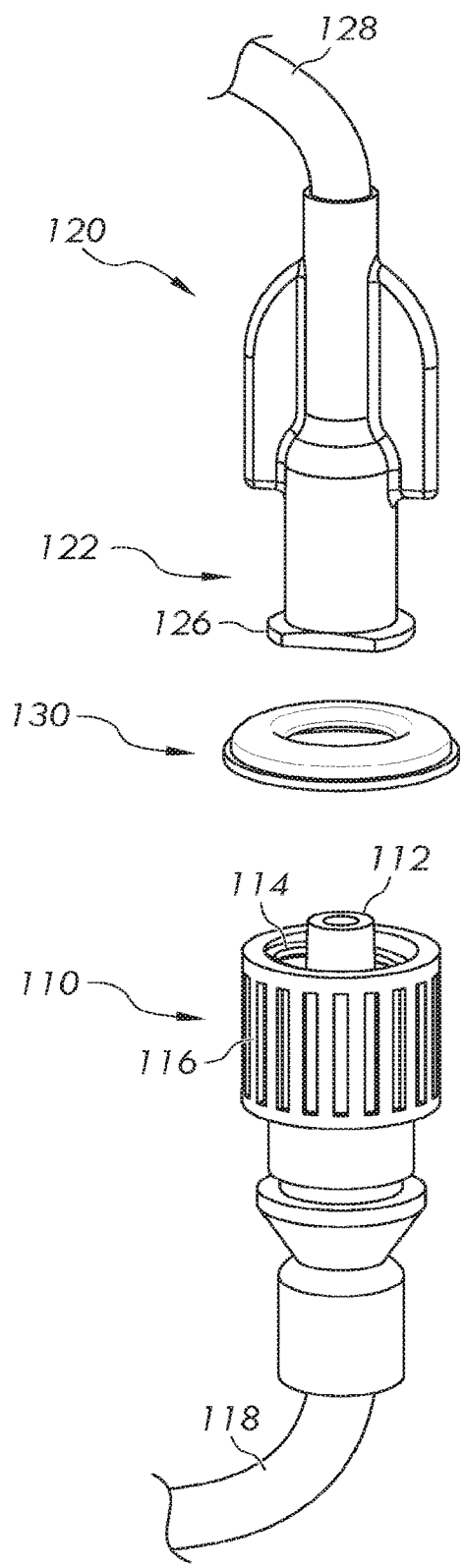
FIG. 3A is an assembly drawing of the system for enhanced sealing of coupled medical fluid lines of FIG. 1, illustrating a lug style lock element, according to an embodiment of the present disclosure.

FIG. 3A is an assembly view of the system 100 for enhanced sealing of coupled medical fluid and vascular access lines of FIG. 2, according to an embodiment of the present disclosure. As above, the system 100 may include the male fitting 110, the female fitting 120, and the annular collar seal 130. Here, the female fitting 120 is of a first exemplary type (lug).

The male fitting 110 may include a male connector 112, a locking collar 116 and a female lock element 114 fixed to the locking collar 116, the female lock element circumscribing the male connector 112, for example, on an interior surface of the locking collar 116. When assembled, the male connector 112 may be fluidly couplable to a first fluid line 118.

The female fitting 120 may include a female connector 124, a connector guide 122 extending radially and axially from the female connector, and a male lock element 126 fixed to the connector guide axially opposite the female connector 124 and extending radially outward from the connector guide 122, the female connector fluidly coupled to a second fluid line 128 and configured to sealingly mate with the male connector 112, the male lock element 126 configured to removably couple with the female lock element 114. According to one embodiment, the male lock element 126 may be configured as a lug coupling such that it may removably couple with the female lock element 114 via insertion and 90 degree locking rotation, or another toolless locking technique.

Figure 3B:
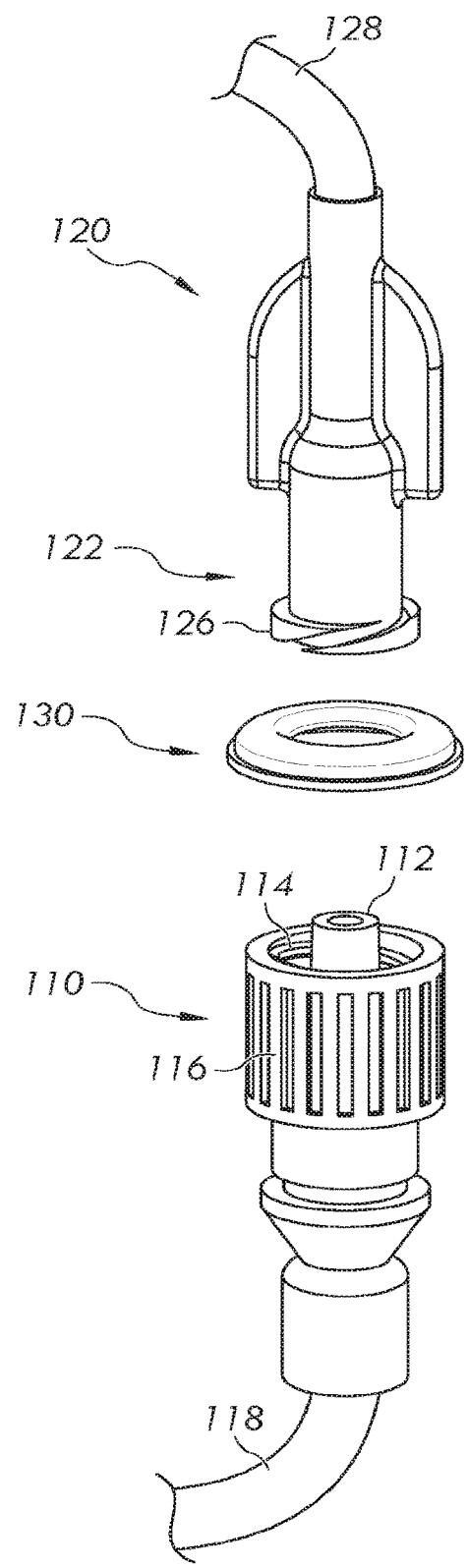
FIG. 3B is an assembly drawing of the system for enhanced sealing of coupled medical fluid and vascular access lines, illustrating a screw style lock element, according to another embodiment of the present disclosure.

FIG. 3B is an assembly view of the system 100 for enhanced sealing of coupled medical fluid lines, according to another embodiment of the present disclosure. As above, the system 100 may include the male fitting 110, the female fitting 120, and the annular collar seal 130. Here, the female fitting 120 is of a second exemplary type (screw). In particular, as shown, the male lock element 126 may be configured as a screw coupling such that it may removably couple with the female lock element 114 via screw motion.

Figure 4:
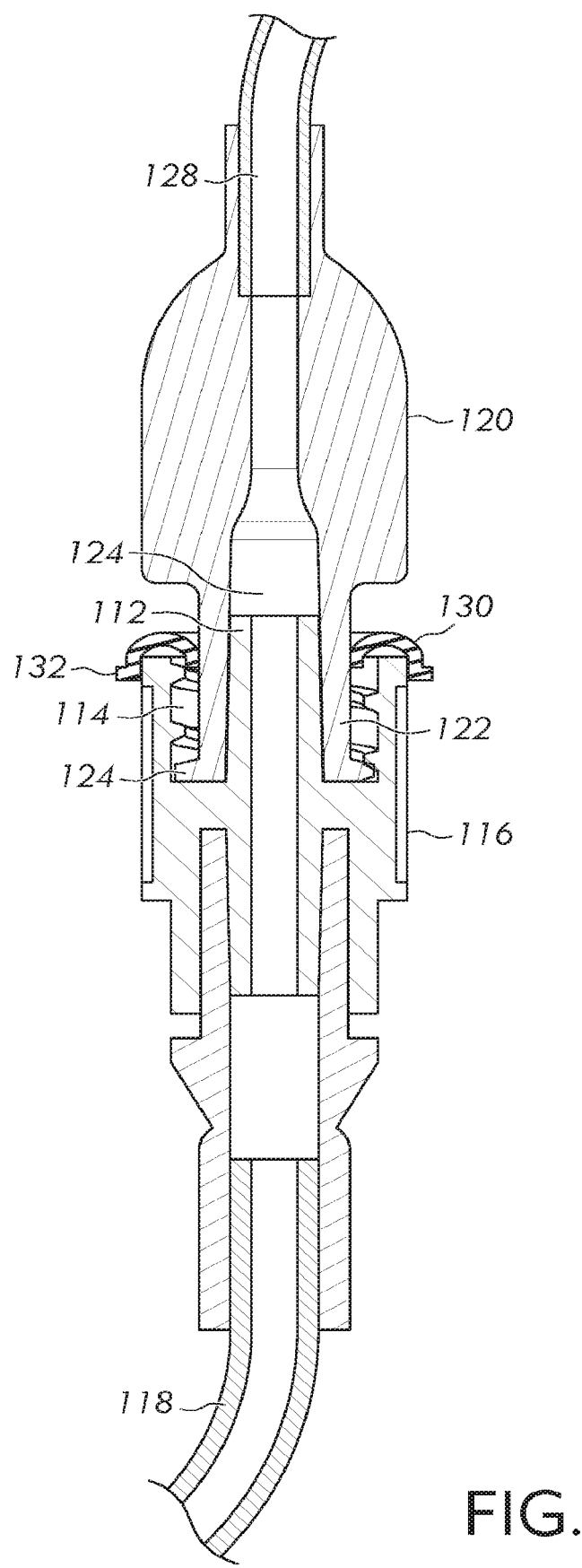
FIG. 4 is a cutaway view of the system for enhanced sealing of coupled medical fluid and vascular access lines of FIG. 1, according to an embodiment of the present disclosure.

FIG. 4 is a section view of the system 100 for enhanced sealing of coupled medical fluid lines of FIG. 2, according to an embodiment of the present disclosure. As depicted, the fluidly coupled connection between the first fluid line 118, the male connector 112, the female connector 124 and the second fluid line 128 may be appreciated.

The outer sealing lip 132 of the annular collar seal 130 is shown circumscribing and sealing the locking collar 116 of the male fitting 110 and also sealing a perimeter of the connector guide 122 of the female fitting 120. The outer sealing lip 132 may be configured to provide enhanced sealing of the male Luer lock connection.

Figure 5:
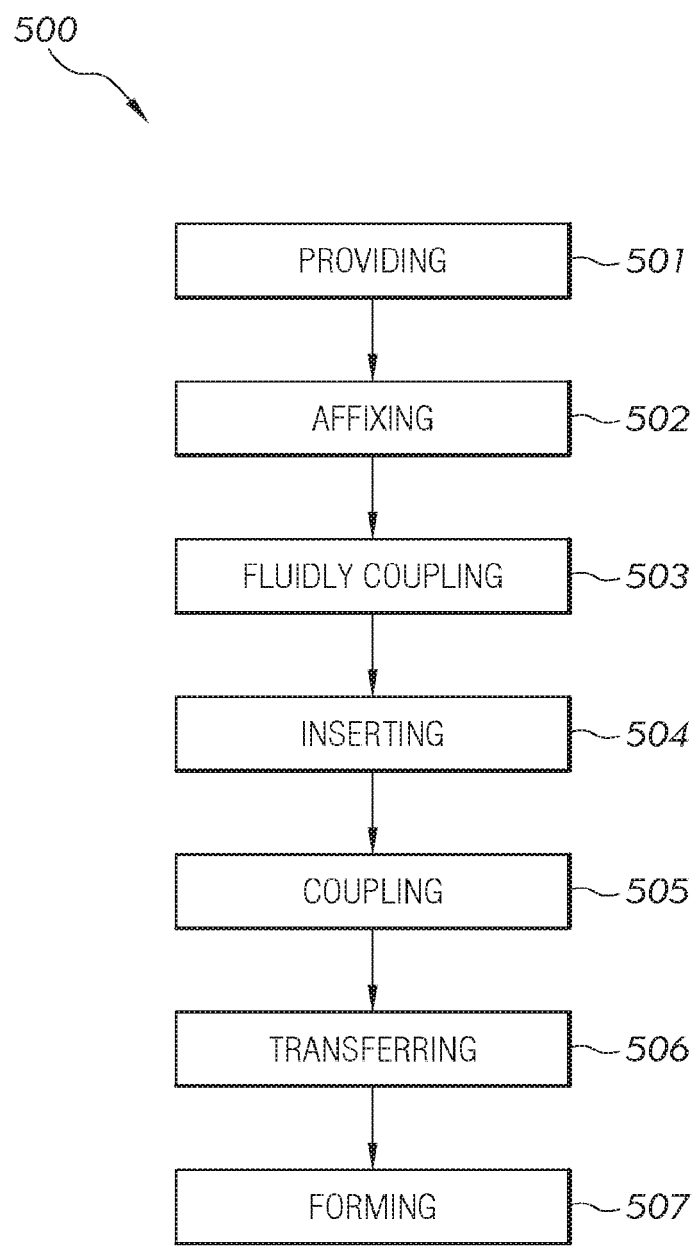
FIG. 5 is a flow diagram illustrating a method for enhanced sealing of coupled medical fluid and vascular access lines having a threaded connection, according to an embodiment of the present disclosure.

FIG. 5 is a flow diagram illustrating a method for enhanced sealing of coupled medical fluid and vascular access line according to an embodiment of the present disclosure. In particular, the method for enhanced sealing of coupled medical fluid lines, including vascular access, drainage, and other lines 500 may include one or more components or features of the system for enhanced sealing of coupled medical fluid lines 100 as described above.

As illustrated, the method for using the system for enhanced sealing of coupled medical fluid lines 500 may include the steps of: step one 501, providing a system for enhanced sealing of coupled medical fluid lines, the system including a male Luer lock fitting 110, a female Luer lock fitting 120, and an annular collar seal 130, the male Luer lock fitting 110 including a male connector 112, a locking collar 116, and a female lock element 114 fixed to the locking collar, the female Luer lock fitting 120 including a female connector 124, a connector guide 122 extending radially and axially from the female connector, and a male lock element 126 fixed to the connector guide 122 axially opposite the female connector and extending radially outward from the connector guide, and the annular collar seal 130 affixable to locking collar 116 of the male fitting 110 and configured to permit passage of the connector guide 122 and the male lock element 126 of the female Luer lock fitting 120 into the locking collar 116 of the male Luer lock fitting 110, and further configured to seal against the connector guide 122 after said passage of the connector guide and the male lock element 126; step two 502, affixing the annular collar seal 130 to the male Luer lock fitting such that the annular collar seal seals against the locking collar 116; step three 503, fluidly coupling a first medical fluid line 128 to the male connector 112 of the male Luer lock fitting 110 and a second medical fluid line 118 to the female connector 124 of the female Luer lock fitting; step four 504, inserting the connector guide 122 and the male lock element 126 of the female Luer lock fitting 120 through the annular collar seal 130 and onto the male Luer lock fitting 110; step five 505, coupling the male lock element 126 of the female Luer lock fitting 120 with the female lock element 114 of the male Luer lock fitting 110; and step six 506, transferring a fluid between the first medical fluid line 128 and the second medical fluid line 116 via the male connector 112 of the male Luer lock fitting 110 and the female connector 124 of the female Luer lock fitting 120. According to one embodiment, the method 500 may further include an additional step seven 507, forming a persistent seal between the annular collar seal and the male Luer lock fitting via at least one of a polymer weld or an adhesive bond.

It should be noted that step seven 507 is an optional step and may not be implemented in all cases. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for using the system for enhanced sealing of coupled medical fluid lines are taught herein.

The seal 130 may have over shapes and sizes. For example, the seal 130 shown herein includes lips 132. The seal 130 is not required to have lips 132. Alternatively, the seal 130 could be provided without lips 132, or the lips 132 could be positioned on an inner surface of the seal 130. Multiple lips positioned adjacent one another could be provided to aid in sealing. The seal is shown as having an arcuate cross-sectional structure. Other shapes could alternatively be used. For example, it is not absolutely required that the seal have an arcuate underlying shape. The seal could be flat, if desired, or have other shapes, such as rectangular or triangular cross-sections, among other shapes. Where a flat seal is used, the seal may be pressed down by another mechanism or integral member to hold the seal in place, such as part of the female connector. There are numerous other shapes for seals that could be utilized without departing from the teachings described herein, which concern using a polymeric sealing mechanism to deter the entry of foreign objects into a connector.

The seal 130 may be bonded or otherwise affixed to the connector. For example, the seal 130 could be bonded to the male connector.

The seal 130 could be formed as a permanent part of the connector, so that it is molded into the connector. This may prevent the seal 130 from moving or breaking lose. The seal 130 could be made a permanent part of the male connector 110, for example. Alternatively, the seal 130 could be used as a retrofit to existing connectors to aid in sealing with existing connectors. The seal 130 may simply seat on top of the male connector 110, as shown in FIG. 4. The seal 130 may have an inner dimension that is greater than the width of the female hub 120 so that action between the female connector 120 and the seal 130 can serve to seal off the entrance of the female connector 120.

In an alternative embodiment, the seal 130 may be impregnated or coated with a material or made with a "smart material" to make the seal more aseptic. For example, the seal 130 could be made of intelligent or responsive materials that are designed to have one or more properties that can significantly change in a controlled fashion based upon external stimuli, such as stress, moisture, light, temperature, PH, or chemical compounds.

One type of material that could be used is a hydrochromic material, which changes color when it comes into contact with moisture or a liquid. Hydrochromic ink, or other types of materials that will change color when contacted with water or moisture, may be used. This would signal to a caretaker that the connector has been exposed to a foreign liquid and that it may be beneficial to the patient to change the connector to avoid the possibility of infection. Other types of color changing materials, additives, or coatings may be used with the seal.

The seal 130 may be coated with chlorhexidine, silver sulfadiazine, or antibiotics, or be silver ion impregnated for further antimicrobial or antibiotic protection. Chlorhexidine is a disinfectant and antiseptic that is used for skin disinfection before surgery and to sterilize surgical instruments. Use of chlorhexidine may aid in deterring infection even if moisture or foreign bodies are able to pass by the seal. Silver sulfadiazine is used to prevent and treat wound infections in patients. It is an antibiotic and works to kill bacteria and prevent growth. Antibiotics are medicines that inhibit the growth of or destroy microorganisms. Silver ions and other silver compounds have an oligodynamic effect and are toxic for bacteria, algae and fungi. The antibacterial action of silver is dependent on the silver ion. The effectiveness of silver compounds as an antiseptic is based on the ability of the silver ion to irreversibly damage key enzyme systems in cell membranes of pathogens. It is known that the use of an electrical field can also improve the properties of silver ion.

Other types of materials or coatings can be used for the seal to provide additional antibacterial, antimicrobial, antiviral, and/or antibiotic properties, among other properties useful in a medical setting.

A system for enhanced sealing of coupled medical lines includes a male fitting 110, a female fitting 120, and a flexible collar seal 130. The male fitting 110 is made of medical grade materials and includes a male connector for fluidly coupling to a first line. The female fitting 120 is made of a medical grade material and includes a female connector for fluidly coupling to a second line. The female connector 120 is configured to mate with the male connector 110. The flexible collar seal 130 is made of a medical grade polymer that is coupled to one or both of the male fitting 110 and the female fitting 120. The seal 130 provides a sealing function to an open end of one or both of the male fitting 110 and the female fitting 120.

The seal 130 may be affixed or bonded to the associated connector. The seal 130 may have an outer sealing lip 132 and an inner sealing lip 132. The outer sealing lip 132 may be configured to circumscribe and seal against the male fitting 110. The inner sealing lip 132 may be configured to deformably permit passage of the female fitting 120 through the inner sealing lip 132.

The male fitting 110 may be a male end of a luer lock. The female fitting 120 may be a female end of a luer lock. The male fitting 110 may be a male end of a lug lock and the female fitting 120 may be a female end of a lug lock. The male fitting 110 may be a male end of a screw thread and the female fitting 120 may be a female end of a screw thread.

The system may comprise multi-lumen connectors. The medical grade materials may include at least one thermoplastic elastomer, a silicone, or a styrene block copolymer.

The inner sealing lip 132 may exert a compressive force to create a compressive seal between the male fitting 110 and the female fitting 120. The seal 130 may have an arcuate cross-sectional shape. The outer sealing lip 132 may be sealed to the male fitting 110 via a polymer weld, an adhesive bond, a compressive spring force seal, or a combination thereof. The seal 130 may have one or more of anti-microbial, anti-bacterial, or anti-fungal properties. The seal 130 may be impregnated or coated with one or more of anti-bacterial, anti-microbial, or anti-fungal materials. The seal 130 may be configured to provide an indicating function that indicates when the seal 130 has encountered moisture.

The seal 130 may be coated with a color-changing material. The seal 130 may be made in whole or in part of a color-changing material. The color changing material changes color when it has encountered a liquid. The color changing material may be a hydrochromic material.

In another embodiment, a connector element for medical use includes a male connector and a seal. A female connector has an opening for receiving the male connector. The seal is coupled to the male connector. The male connector is inserted into the female connector. When the male connector is inserted in the female connector, the seal deters the entry of foreign materials into the connector element.

The seal may have color-changing properties that signal when the seal has encountered a liquid. The color changing properties are provided by a coating of a hydrochromic material. The seal may be made in whole or part of a hydrochromic material. The seal may have one or more of anti-bacterial, anti-microbial, or anti-fungal properties. The seal may have at least one sealing lip for sealing the opening of the female connector. The seal may be flexible and deformable.

The presently described invention concerns medical connections with a seal that can be used in different types of delivery systems. Some examples of delivery systems that may derive a benefit from the invention include vascular, enteral, respiratory, epidural, intrathecal medical devices, drainage systems, as well as their components and accessories. The invention can be used with single devices or with devices that have multiple lumens. The invention may also be useful in implanted ports to deter entry of foreign liquids into the line.

Certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The embodiments of the disclosure described herein are exemplary and numerous modifications, variations and rearrangements can be readily envisioned to achieve substantially equivalent results, all of which are intended to be embraced within the spirit and scope of the disclosure.

The term "substantially," if used herein, is a term of estimation.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. A system for enhanced sealing of coupled medical lines, the system comprising:
   a male fitting made of medical grade materials and including a male connector for fluidly coupling to a first line;
   a female fitting made of medical grade materials and including a female connector for fluidly coupling to a second line and configured to mate with the male connector; and
   an external, self-retained flexible collar seal made of a medical grade polymer normally seated around an exterior end and exterior surface of at least the male fitting,
   wherein the seal provides a sealing function to an open end of one or both of the male fitting and the female fitting and the collar seal is self-retained so that no additional member is required to retain the seal on the male fitting during use.

2. The system of claim 1, wherein the seal is normally affixed or bonded to the associated connector and the seal is annular.

3. A system for enhanced sealing of coupled medical lines, the system comprising:
- a male fitting made of medical grade materials and including a male connector for fluidly coupling to a first line;
- a female fitting made of medical grade materials and including a female connector for fluidly coupling to a second line and configured to mate with the male connector; and
- a flexible collar seal made of a medical grade polymer coupled to at least the male fitting,
- wherein the seal provides a sealing function to an open end of one or both of the male fitting and the female fitting,
- wherein the seal has an outer sealing lip and an inner sealing lip, with the outer sealing lip configured to circumscribe and seal against the male fitting and the inner sealing lip configured to deformably permit passage of the female fitting through the inner sealing lip.

4. The system of claim 3, wherein the male fitting is a male end of a Luer lock and the female fitting is a female end of a Luer lock; or the male fitting is a male end of a lug lock and the female fitting is a female end of a lug lock; or the male fitting is a male end of a screw thread and the female fitting is a female end of a screw thread.

5. The system of claim 3, wherein the system comprises multi-lumen.

6. The system of claim 3, wherein the medical grade materials include at least one of a thermoplastic elastomer, a silicone, or a styrene block copolymer.

7. The system of claim 3, wherein the inner sealing lip exerts a compressive force to create a compressive seal between the male fitting and the female fitting.

8. The system of claim 3, wherein the seal has an arcuate cross-sectional shape.

9. The system of claim 3, wherein the outer sealing lip is sealed to the male fitting via a polymer weld, an adhesive bond, or a combination thereof.

10. The system of claim 3, wherein the seal has one or more of anti-microbial, anti-bacterial, or anti-fungal properties.

11. The system of claim 10, wherein the seal is impregnated or coated with one or more of anti-microbial, anti-bacterial, or anti-fungal materials.

12. The system of claim 3, wherein the seal is configured to provide an indicating function that indicates when the seal has encountered moisture.

13. The system of claim 12, wherein the seal is coated with a color-changing material, and/or the seal is made in whole or in part of a color-changing material, wherein the color-changing material changes color when it is or has encountered a liquid.

14. The system of claim 13, wherein the color changing material is a hydrochromic material.

15. A connector element for medical use comprising:
- a male connector for mating with an opening of a female connector, said male connector having an opening; and
- an external self-retained seal seated around and covering an exterior surface of an exterior end having the opening of the male connector,
- wherein when the male connector is inserted in an opening of the female connector, the connector element is sealed to deter the entry of foreign materials into the connector element, and the seal is self-retained so that no additional member is needed to retain the seal on the male connector.

16. The connector element of claim 15, wherein the seal has color-changing properties that signal when the seal has encountered a liquid.

17. The connector element of claim 16, wherein the color changing properties are provided by a coating of a hydrochromic material, and/or by a seal that is made in whole or part of a hydrochromic material.

18. The connector element of claim 15, wherein the seal has one or more of anti-bacterial, anti-microbial, or anti-fungal properties.

19. The connector element of claim 15, wherein the seal has at least one sealing lip for sealing the opening of the connector element.

20. The connector element of claim 15, wherein the seal is flexible and deformable.

21. A seal for enhanced sealing of coupled medical lines that include a male fitting made of medical grade materials and a female fitting for mating with the male fitting made of medical grade materials, the seal comprising:
- a flexible collar seal having an outer sealing lip and an inner sealing lip, with the outer sealing lip configured to circumscribe and seal against the male fitting and the inner sealing lip configured to deformably permit passage of the female fitting through the inner sealing lip, said collar seal made of a medical grade polymer shaped to seat around en an exterior surface of a male or a female fitting, wherein the collar seal has color changing properties that signal when the seal has encountered a liquid, with the color changing properties being provided by a coating of a hydrochromic material, and/or by a collar seal that is made in whole or part of a hydrochromic material.

* * * * *